United States Patent [19]

Beachey et al.

[11] Patent Number: 4,919,930
[45] Date of Patent: Apr. 24, 1990

[54] SYNTHETIC M PROTEINS-STREPTOCOCCI TYPE 5

[75] Inventors: Edwin H. Beachey; James B. Dale, both of Memphis, Tenn.

[73] Assignee: University of Tennessee Research Corporation, Knoxville, Tenn.

[21] Appl. No.: 858,436

[22] Filed: May 1, 1986

Related U.S. Application Data

[60] Continuation-in-part of Ser. No. 739,963, May 31, 1985, abandoned, and a continuation-in-part of Ser. No. 700,625, Feb. 12, 1985, Pat. No. 4,597,967, which is a division of Ser. No. 503,273, Jun. 10, 1983, Pat. No. 4,521,334.

[51] Int. Cl.$^5$ .................... A61K 39/09; A61K 37/02; C07K 7/08; C07K 7/10
[52] U.S. Cl. ......................................... 424/88; 514/12; 514/13; 514/14; 514/15; 530/324; 530/326; 530/327; 530/328; 530/345; 530/403; 530/806
[58] Field of Search ............... 530/324, 326, 327, 328, 530/345, 403, 806; 514/12, 13, 14, 15; 424/88

[56] References Cited

U.S. PATENT DOCUMENTS

| | | | |
|---|---|---|---|
| 4,284,537 | 8/1981 | Beachey | 424/85 |
| 4,454,121 | 6/1984 | Beachey | 514/12 |
| 4,521,334 | 6/1985 | Beachey | 424/88 |
| 4,597,967 | 7/1986 | Beachey | 530/324 |
| 4,695,562 | 9/1987 | Beachey et al. | 530/326 |
| 4,705,684 | 11/1987 | Beachey | 530/326 |

OTHER PUBLICATIONS

Dale et al., Journal of Experimental Medicine, vol. 158, pp. 1727–1732, (1983).
Beachey et al., The Journal of Immunology, vol. 136, No. 6, pp. 2287–2292, (1986).
Beachey et al., The Journal of Experimental Medicine, vol. 145, pp. 1469–1483, (1977).
Manjula et al., The Journal of Biological Chemistry, vol. 259, No. 6, pp. 3686–3693.
Beachey, E. H., G. L. Campbell, and I. Ofek 1974, Infect. Immun. 9:891.
Beachey, E. H., J. M. Sever, and A. H. Kang 1978, Proc. Natl. Acad. Sci. USA 75:3163.
Beachey, E. H., G. H. Stollerman, R. H. Johnson, I. Ofek, and A. L. Bisno, 1979, J. Exp. Med. 150:862.
Manjula, B. M., A. Seetharma-Acharya, S. M. Mische, T. Fairwell, and V. A. Fischetti 1984, J. Biol. Chem. 259:3686.
Dale, J. B. and E. H. Beachey 1982, J. Exp. Med. 156:1165.
Dale, J. B. and E. H. Beachey 1982, Trans. Assoc. Am. Physicians 95:286.
Dale, J. B. and E. H. Beachey 1985, J. Exp. Med. 161:113 162:583.
Beachey, E. H., J. M. Seyer, and A. H. Kang 1980, J. Biol. Chem. 255:6284.
Beachey, E. H., J. M. Seyer, J. B. Dale, W. A. Simpson, and A. H. Kang, 1981, Nature 292:457–459.
Beachey, E. H., J. M. Seyer, J. B. Dale, and D. L. Hasty, 1983, J. Biol. Chem. 258:13250.
Beachey, E. H., A. Tatar, J. M. Seyer, and L. Chedid, 1984, Proc. Natl. Acad. Sci. USA, 81:2203–2207.
Seyer, J. M., A. H. Kang, and E. H. Beachey, 1980, Biochem. Biophys. Res. Commun. 92:546.
Dale, J. B., I. Ofek, and E. H. Beachey, 1980, J. Exp. Med. 151:1026.
Hasty, D. L., E. H. Beachey, W. A. Simpson, and J. B. Dale 1982, J. Exp. Med. 155:1010.
Dale, J. B. and E. H. Beachey, 1984, Infect. Immun. 46:267.
Manjula, B. M. and V. A. Fischetti 1980, J. Immunol. 124:261.
Phillips, G. N., P. F. Licker, C. Cohen, B. M. Manjula, and V. A. Fischetti 1981, Proc. Natl. Acad. Sci. USA, 78:4689.
Hopp et al., Proc. Natl. Acad. Sci. USAm, vol. 78, No. 6, pp. 3824–3828, (Jun. 1981).
E. H. Beachey, J. M. Seyer and A. H. Kang, 1978, Proc. Natl. Acad. Sci. UAA, 75:3163.

Primary Examiner—Delbert R. Phillips
Assistant Examiner—Christina Chan
Attorney, Agent, or Firm—Weiser & Stapler

[57] ABSTRACT

Synthetic peptide segments of protein Pep M5 containing epitopes capable of evoking type specific opsonic antibodies against streptococci when covalently linked to a protein carrier.

28 Claims, 2 Drawing Sheets

SYNTHETIC M PROTEINS-STREPTOCOCCI TYPE 5

This invention was made with Government support under research funds from the U.S. Veterans Administration and by research grants A1-10085 and AI-13550 from the U.S. Public Health Service. The Government has certain rights in this invention.

This application is a continuation-in-part of U.S. application Ser. No. 739,963, now abandoned, entitled Streptococcal M Protein and Compositions and Use filed May 31, 1985, wherein Edwin H. Beachey, Andre Tartar, Helene Gras-Masse, Michel Jolivet, Francoise Audibert and Louis Chedid are named inventors and also a continuation-in-part of U.S. application Ser. No. 700,625 entitled Synthetic Polypeptide Fragments, filed Feb. 12, 1985 U.S. Pat. No. 4,597,967 issued July 1, 1986 wherein Edwin H. Beachey is named inventor and which is a divisional application of U.S. application Ser. No. 503,273, filed June 10, 1983 now U.S. Pat. No. 4,521,334, issued June 5, 1985. The parent applications are incorporated herein by reference.

This invention relates to peptide fragments of the M protein of S. pyogenes. More particularly, the invention relates to synthetic immunogenic peptides which are fragments of M5, M6 and M24 proteins and which are able to inhibit opsonic antibodies obtained from rabbits immunized with the respective pep M5, M6 and M24 molecules.

The invention further relates to haptens which, when linked to a suitable carrier, elicit high titers of type-specific opsonic and bactericidal antibodies in rabbits.

The invention further relates to the synthetic antigen conjugates of these haptens with appropriate carriers which evoke immune responses which are type-specific for type M5, M6 or M24 streptococci, and which are not seroligically cross-reactive with tissue antigens of the human or host heart.

The invention further relates to the biologically active compositions which comprise the synthetic antigen conjugates and a biologically acceptable diluent and which are immunogenic with respect to Streptococcus pyogenes.

The invention further relates to vaccines which comprise the synthetic antigen conjugates which are effective to immunize a patient against Streptococcus pyogenes.

The invention further relates to the method for controlling streptococcal infections in a mammal which comprises administering the biologically active compositions to said mammal.

All references are listed by number at the end of the specification and are incorporated herein by reference.

For over one-half century, attempts have been made to develop safe and effective vaccines against strains of group A streptococci that give rise to rheumatic fever and rheumatic heart disease (1, 29). Most of these efforts have been frustrated by severe toxic reactions to almost any streptococcal product introduced into the human host. Some of these products have been shown to give rise to antibodies that cross-react with host tissues, especially the heart (30, 31). Although it has long been established that the M protein on the surface of group A streptococci contains the protective antigen(s) of these organisms, the fear has been that the isolated M protein may be associated with potentially harmful tissue cross-reactive antigens that give rise to, rather than prevent, rheumatic fever. This fear has been perpetuated by the finding that certain rheumatogenic streptococci produce M proteins that are closely associated with a heart cross-reactive antigen (3, 2). Indeed recently it has been established that one of the M protein molecules contains, within its covalent structure, an epitope that elicits a protective anti-streptococcal antibody that also cross-reacts with a sarcolemmal protein of human heart tissue (7).

Recently Audibert et al actively immunized laboratory animals against diphtheria toxin using a chemically synthesized oligopeptide (33). This work does not show, however, that a synthetic peptide antigen can raise antibodies which promote phagocytosis and killing of a bacterial pathogen.

U.S. Pat. No. 4,284,537, to E. Beachey, issued Aug. 18, 1981, discloses the amino acid sequence of two peptide fragments derived from type 24M protein. It also discloses that each of these natural fragments, when covalently linked to a carrier such as polylysine, is able to elicit type-specific opsonic antibodies effective against Streptococcus pyogenes. Each of these fragments is a natural extract, and each contains 35 amino acids.

The above-referred to patent, ('537) describes inter alia, a synthetic peptide (S-CB7) and that one of the protective determinants is located in a specific fragment of S-CB7 of type 24M protein which contains only twelve amino acid residues (S-CB7(18-29)). S-CB7, as described, differs from the native CB-7 fragment in that the COOH-terminal residue of S-CB7 is methionine, in contrast to homoserine. The specification also teaches and described covalently linked conjugates of S-CB7 and appropriate hapten carriers, natural, like BSA or OVA or synthetic, like polylysine. Further details about this work have been published in Nature on July 30, 1981, by Beachey et al, 292, pages 457-459 (12).

U.S. Pat. No. 4,521,334, entitled Synthetic Polypeptide Fragments, to Edwin H. Beachey, issued June 4, 1985, discloses the amino acid sequence of three peptide fragments CB3, CB4, and CB 5, and 35 and 37 amino acid sequences of type 24M which contain antigenic determinants corresponding to the antigenic determinants contained in CB3-CB7. It also discloses that these fragments, when covalently linked to a carrier such as polylysine, are able to elicit type-specific opsonic antibodies effective against Streptococcus pyogenes. The patent further discloses a peptide fragment of type 5M protein identified as S pep M5(1-20). This synthetic peptide elicits opsonic antibodies when covalently linked to a carrier.

U.S. application Ser. No. 739,963 entitled "Biologically Active Hybrid Peptides of Streptococcal M Protein and Compositions and Use" to Beachey et al, filed May 31, 1985, disclosed peptide sequences containing fragment of M5, M6, and M24 proteins which are able to elicit opsonic and bactericidal antibodies to Streptococcus pyogenes which are not serologically cross-reactive with tissue antigens of the human or host heart. In particular a peptide identified as M5(1-10)-M6(1-11)-M24(1-12) is disclosed. This peptide elicits opsonic antibodies against M5, M6 and M24 protein.

Notwithstanding these advances, there remains a serious need, as yet unfilled, to identify and synthesize protective regions of other rheumatogenic serotypes so that a combination of protective peptides could be incorporated into a single vaccine to evoke protective immunity against many rheumatogenic serotypes of group A streptococci without causing tissue cross-reactive adverse reactions. The problem has been described by Hasty et al, (22). Another attempt in predicting protein antigenic determinants from amino acid sequences (including the streptococcal M protein) has been published by Hopp et al, (34). The present invention marks another forward step and provides another advance in the medical sciences, particularly in the control of streptococcal infections.

Accordingly, it is a primary object of the invention to provide peptide fragments which are useful as haptens which when linked to a suitable carrier are able to elicit opsonic antibodies obtained from a mammal which has been immunized with uncleaved pep M5, M6 or M24 molecules.

Another object of the invention is the production of biologically active compositions which are immunogenic with respect to S. pyogenes.

Another object of the invention is to provide for a method of controlling streptococcal infections in a mammal.

Other worthwhile objects will become apparent from the disclosure herein. Other features and advantages of the invention will appear from the examples which follow and by referring to the appended drawing in which:

FIG. 1 shows the peptide specificity of pep M5 reactive antibodies raised against SM5(1-35) as determined by inhibition of ELISA. A constant dilution of anti-SM5(1-35) was incubated with increasing concentrations of pep M5 (●), SM5(1-35) (■), SM5(14-35) (■), SM(21-35) (△) or SM5(26-35) (o) used as soluble inhibitors of antibody binding to the natural pep M5 antigen, which was immobilized on plastic plates. The highest concentration of the synthetic peptides was 40 nM, while the highest concentration of pep M5 was 10 ug/ml.

FIG. 2 shows ELISA inhibition by the subpeptide SM5(14-26) of pep M5 reactive antibodies raised against SM5(1-35). A constant dilution of anti-SM5(1-35) was incubated with increasing concentrations of either pep M5 (●) or SM5(14-26) (o) as soluble inhibitors of antibody binding to pep M5, which was the solid phase antigen. The highest concentration of SM5(14-26) was 40 nM and the highest concentration of pep M5 was 10 ug/ml.

The mechanism whereby streptococcal infections give rise to complications such as rheumatic fever have remained, to a large extent, unexplained to date. Because the sera of some patients with rheumatic fever show serological cross-reactivity between heart tissue antigens and certain streptococcal antigens, it has been feared that immunization with intact M-protein vaccines may lead to rheumatic heart disease. See, for instance, Stollerman, *Rheumatic Fever and Streptococcal Infection,* supra. It has been observed that rabbits and mice immunized with cyanogen bromide fragments (CB6 or CB7) of type 24M protein containing only 35 amino acid residues each developed opsonic and protective antibodies against type 24 streptococci.

Recently, it has been demonstrated that serotypes 5, 6, and 19M proteins share antigenic determinants with human sarcolemmal membranes (7-9) as well as with cardiac myosin (10). Because the M protein contains the only protective antigenic determinants of virulent group A streptococci ((1), it has become imperative to carefully identify the regions of the molecule that contained protective as opposed to cardiac tissue cross-reactive epitopes.

The notion that one may be able to evoke protective immunity with peptide fragments of various regions of the M protein molecule was first suggested by studies of the protective immunogenicity of large polypeptide fragments extracted by limited digestion of streptococcal cells with dilute solutions of pepsin as pH 5.8 (2, 3, 17, 26). These fragments, ranging in $M_r$ from 19,000 to 33,500, were shown to be highly immunogenic, stimulating protective antibodies against the related streptococci in laboratory animals (22), as well as in humans (35). Subsequent studies of yet smaller fragments derived from type 24M protein by cyanogen bromide cleavage demonstrated that the five repeating 35-residue fragments, as well as a 90-residue fragment each contained protective epitopes, and when covalently linked to polylysine had the capacity to evoke type-specific protective immunity against type 24 streptococci (11, 12, 36). Moreover, chemically synthesized copies of the 35-residue fragments 3 and 7 (S-CB3 and S-CB7, respectively), as well as subpeptide fragments of S-CB7 containing as few as 13 amino acid residues of type 24M protein had the capacity, when linked to a carrier, to evoke type-specific protective immunity (12-14).

Having established the principle of the protective immunogenicity of small peptide fragments of the repeating covalent structure of type 24M protein, a serotype of which the pepsin-extracted polypeptide fragment is devoid of tissue cross-reactive antigens, studies have turned to the serotypes of M proteins shown to contain such cross-reactive determinants. It has been shown that a chemically synthesized peptide copy of the first 20 residues of the $NH_2$-terminus of type 5M protein evoked type-specific protective antibodies in rabbits without stimulating heart cross-reactive antibodies (15, U.S. Pat. No. 4,521,334).

The ability to identify limited regions of M protein molecules that contain protective epitopes, as opposed to tissue cross-reactive and nonprotective epitopes, may be an important step in developing safe and effective group A streptococcal vaccines. It has recently been shown that pepsin extracted M protein fragments from types 5, 6, and 19 streptococci contain epitopes that cross-react with sarcolemmal membrane proteins of human myocardium (7-9) and myosin (10), thus making the pep M proteins unsuitable for vaccine preparation. Previous studies have been designed to determine the minimum peptide structures of several M proteins that retain protective immunogenicity and not tissue cross-reactivity (11-16). Chemically synthesized peptides of type 24 protein, ranging in size from 13 to 35 amino acid residues, were found to evoke protective antibody responses in laboratory animals (12,14). Most recently, synthetic peptides representing the amino terminus of type 6M protein were also shown to produce protective, and not heart cross-reactive, immunity (16). Similar studies have been performed with synthetic peptides of type 5M protein (15) which showed that S-M5(1-20) contained protective epitopes, whereas S-M5(20-40) did not.

The present work was undertaken to identify precisely the primary structure of the amino terminus of type 5M protein that contains protective antigenic determinants. It was first shown that S-M5(1-35) was immunogenic and evoked opsonic antibodies in rabbits. Using overlapping peptides, three immunologically distinct regions of S-M5(1-35) were identified: the amino terminus, which did not evoke M5 reactive antibodies; the carboxy terminus, which evoked M5 antibodies that were non-opsonic; and the region between residues 14 and 26, which contained all of the protective epitopes of S-M5(1-35). In addition, S-M5(14-26)C, when linked to an appropriate carrier molecule, evoked opsonic antibodies against type 5 streptococci. Thus, by using a set of overlapping synthetic peptides representing type 5M protein, a discrete region of the molecule, composed of only 13 amino acids has been identified, that retains protective immunogenicity and does not evoke host tissue cross-reactive antibodies.

The three immunologically different regions of S-M5(1-35) were detected by methods designed to determine the functional activity of anti-peptide antibodies. The titers of S-M5(1-35) antisera against the synthetic peptide were consistently higher than those against pep M5, the natural protein, suggesting that at least some of the antibodies were peptide-specific. This was confirmed by ELISA inhibition experiments which showed that not all of the S-M5(1-35) antibodies were inhibited by pep M5. The finding that opsonic antibodies raised against whole type 5 streptococci that were affinity purified with S-M5(1-35) were completely inhibited by S-M5(14-26) confirms the immunodominance of this region of the amino terminus and suggests that the findings were not an artifact of the synthetic immunogen or the coupling procedure.

Recent evidence suggests that the ability of antibodies evoked by synthetic peptides to recognize epitopes within the natural protein is partly a function of the atomic mobility of the structure in its native state (24). Although such data are not yet available for M protein molecules, Manjula and Fischetti have previously shown that a consistent structural feature among the M proteins sequenced thus far is a seven-residue periodicity with respect to polar and noncharged amino acids which would predict an α-helical secondary structure (25-27). The α-helical potential of pep M5 begins at residues 14-17 and is particularly high between residues 27 and 54 (25, 28). The opsonic epitopes of S-M5 (1-35) corresponded to the region in pep M5 (residues 14-26) that displays moderate α-helical potential (25, 28), suggesting that this secondary structural configuration may be related to immunodominance and the ability of anti-peptide antibodies to react with the natural protein. Although the amino terminal 13 amino acid residues of S-M5(1-35) did not evoke opsonic antibodies, a synthetic peptide copy of the first 10 amino acids of pep M5 evokes opsonic antibodies, indicating that this portion of the M protein molecule is not devoid of protective epitopes.

The data support the concept that the amino terminal regions of M proteins evoke opsonic antibodies (15, 16). Thus far, none of the synthetic peptides of these M proteins has produced cross-protective antibodies. An effective streptococcal vaccine most likely will need to be formulated from protective fragments of M proteins representing as many as 15 to 20 "rheumatogenic" serotypes of streptococci. The ability to precisely identify protective, as opposed to nonprotective and heart cross-reactive, M protein epitopes allows the disposal of the majority of the molecule, therefore minimizing the total amount of protein injected and reducing the risk of potentially harmful autoimmune reactions.

In accordance with the present invention overlapping peptides copying the NH$_2$-terminal region of type 5M protein have been synthesized. Type 5M serotype has been shown to contain cardiac tissue cross-reactive epitopes (15). Several of the peptides have been found to be immunogenic with respect to S. pyogenes.

As non-limiting examples of this invention, synthetic M5 peptides were prepared. Some of the peptides are designated by the general formula X-Glu-Ala-Leu-Asp-Lys-Tyr-Glu-Leu-Glu-Asn-His-Y wherein
X is Lys, or Ala-Val-Thr-Lys-Gly-Thr-Ile-Asn-Asp-Pro-Gln-Ala-Ala-Lys
and
Y is
Asp
Asp-Cys, or
Asp-Leu-Lys-Thr-Asn-Asn-Glu-Gly-Leu-Lys.

Within the general formula, the synthetic peptides include those labeled as S-M5(1-35), S-M5(14-35), S-M5(14-26) and S-M5(14-26)C.

The amino acid sequence of the synthetic peptide S-M5(1-35) is

Ala—Val—Thr—Lys—Gly—Thr—Ile—Asn—Asp—Pro—Gln—Ala—Ala—Lys—Glu—Ala—Leu—Asp—Lys—Tyr—Glu—Leu—Glu—Asn—His—Asp—Leu—Lys—Thr—Asn—Asn—Glu—Gly—Leu—Lys.

The amino acid sequence of S-M5(14-35) is

Lys-Glu-Ala-Leu-Asp-Lys-Tyr-Glu-Leu-Glu-Asn-His-Asp-Leu-Lys-Thr-Asn-Asn-Glu-Gly-Leu-Lys.

The amino acid sequence of S-M5(14-26) is

Lys-Glu-Ala-Leu-Asp-Lys-Tyr-Glu-Leu-Glu-Asn-His-Asp.

The amino acid sequence of S-M5(14-26)C is

Lys-Glu-Ala-Leu-Asp-Lys-Tyr-Glu-Leu-Glu-Asn-His-Asp-Cys.

The synthetic peptides of the invention also include the M5 peptides labeled as S-M5(21-35), S-M5(26-35) and S-M5(1-10)C.

The amino acid sequence of S-M5(21-35) is

Glu-Leu-Glu-Asn-His-Asp-Leu-Lys-Thr-Asn-Asn-Glu-Gly-Leu-Lys.

The amino acid sequence of S-M5(26-35) is

Asp-Leu-Lys-Thr-Asn-Asn-Glu-Gly-Leu-Lys.

The amino acid sequence of S-M5(1-10) is

Ala-Val-Thr-Lys-Gly-Thr-Ile-Asn-Asp-Pro-Cys.

Other synthetic peptides of the invention include the M6 peptide labeled as S-M6(1-11)C and the M24 peptide labeled as S-M24(1-12)C.

The amino acid sequence of S-M6(1-11) is

Arg-Val-Phe-Pro-Arg-Gly-Thr-Val-Glu-Asn-Pro-Cys.

The amino acid sequence of S-M24(1-12)C is

Val-Ala-Thr-Arg-Ser-Gln-Thr-Asp-Thr-Ser-Glu-Lys-Cys.

The structure of the peptides are also shown in Table I in single letter code (IUPAC-IBU Commission on Biochemical Nomenclature (1968), J. Biol. Chem. 243, 3557-3559) for ease of comparison.

Other amino acid sequences of type 5M protein having ability to elicit opsonic antibodies to type 5M protein when conjugated to a carrier are also within the scope of the invention.

It is also within the scope of the invention that certain amino acids within the peptide sequences can be substituted by other amino acids. For example, in type M5, one or more of the amino acids at position 1, 4, 8, 12 and 30 can be substituted by Thr, Arg, Ser, Arg and Lys, respectively. The resulting amino acid sequences have equivalent ability to elicit opsonic antibodies to type 5M protein. Other amino acids can also be substituted within the sequence.

In accordance with the invention the synthetic peptides are conjugated with hapten carriers. The conjugates are capable of producing immune responses against pep M proteins or whole type streptococci as measured by opsonic antibody and ELISA tests.

When covalently linked to lysylated tetanus toxoid S-M5(1-35), the conjugate evokes significant levels of antibodies against the immunogen and native pep M5 in rabbits. When S-M5(26-35) was conjugated with lysylated tetanus toxoid, the conjugate evokes significant levels of antibodies against S-M5(1-35) and pep M5 in the immune sera in rabbits. When S-M5(14-26)Cys was cross-linked with keyhole lympet hemocyanin, the conjugate evoked singificant levels of antibodies against S-M5(14-26), S-M5(1-35) and pep M5 in rabbits as measured by ELISA.

When rabbits were immunized with an equimolar mixture of S-M5(1-10)C, S-M6(1-11)C and S-M24(1-12)C covalently linked to keyhole lympet hemocyanin the mixture evoked antibodies against types 5, 6 and 24 streptococci in the immune sera in rabbits.

Furthermore, none of the conjugated synthetic peptides raised antibodies that were cross-reactive with human heart tissue.

In accordance with the invention, the carriers which are used to make the conjugate with the peptide sequences of the invention are any "natural" or "synthetic" carrier. The term "carrier" is a recognized term in the art and literature and sometimes is referred to as "coupler" or as "protein carrier". Numerous molecules, especially proteins and polysaccharides, may be coupled covalently to a hapten to act as a carrier. For this purpose, haptens may also be bound to erythrocytes, bacteriophages, artificial or synthetic macromolecules, and even to insoluble carriers. The hapten should posses one or several reactive groups that permit binding (covalent bonds) to carrier functional groups, under physiochemical conditions that maintain the integrity of the hapten structure, and as much as possible, of the carrier protein.

In some cases, binding of hapten to carrier requires mere contact (this is the case for nitrophenyl derivatives); most often, however, a coupling agent is required. When the hapten itself does not possess any reactive group, it may be introduced through a previous reaction. Thus, in order to couple steroids without carboxyl function to proteins, their alcohol function may be transformed into hemisuccinate, which introduces a carboxyl group.

Natural carriers used in accordance with the invention are known and are, typically, tetanus toxoid, keyhole limpet hemocyanin (KLH), BSA or OVA. Synthetic carriers are, typically, polylysine. Hapten carriers are well known in the literature and need not be further described here to one skilled in the art. Generally, these carriers are covalently linked to the protein sequence.

Moreover, it has been found that the coupled antigen can be administered with a natural immunostimulant, preferably complete Freund's adjuvant or a synthetic immunostimulant, preferably of the MDP type, like MDP, its analogs and derivatives in aqueous saline solution, such as phosphate buffered saline ("PBS").

It is contemplated in accordance with the invention that whenever the term "MDP" is used for the synthetic immunostimulant, the term is and does include any synthetic immunostimulant which contains (or encompasses, or includes, etc.) the basic MDP (or the nor-MDP, i.e., 2-(2-acetamido-2-deoxy-D-glucos-3-O-yl-D-propionyl-L-alanyl-D-isoglutamine) structure, which structure has been recognized in the art to be the minimal structure to contribute to immunogenicity. The term "MDP" immunostimulant", or "MDP type" or "nor-MDP type" or MDP analogs and derivatives are to be taken broadly. Such MDP immunostimulants are well known in the literature, which is incorporated by reference and include the following for illustrative purposes. U.S. Pat. Nos. 4,082,735; 4,082,736; 4,153,684; 4,220,637; 4,101,649; 4,186,194; 4,235,771; and the following publications: *Biken Journal,* Vol. 18, 105–111, 1975; *Microbiology* (1977) 388–394; *Cellular Immunology* 21, 243–249 (1976); *Proc. Natl. Acad. Sci. USA,* Vol. 73, No. 7, pps. 2472–2475, July 1976; *Int. J. Peptide Protein Res.,* 9, 1977, pps. 249–257; *Biken Journal,* Vol. 20, pps. 95–103, 1977; *C. R. Acad. Sci. Paris,* t. 285 (Sept. 12, 1977); *Prog. Allergy,* Vol. 25, pps. 63–105 (Karger, Basel 1978); and *Cellular Immunology* 35, pps. 173–179 (1978).

The primary structures of the synthesized overlapping peptides of type M5 protein were determined by automated Edman degradation to assure their identity with the native pep M5 molecule (Table I). All of the peptides were identical to the corresponding regions of the primary structure of pep M5 (17).

Initial experiments were performed to determine the immunogenicity of S-M5(1-35), the longest polypeptide synthesized for the study, and S-M5(26-35), the shortest polypeptide, both of which were covalently linked to tetanus toxoid. All six rabbits immunized with S-M5(1-35) developed significant levels of antibodies against the immunogen and native pep M5, as determined by ELISA (Table II). All six rabbits also developed significant levels of opsonic antibodies against type 5 streptococci, as determined by in vitro opsonophagocytic tests (Table II). None of the immune sera cross-reacted with human heart tissue or myosin, as determined by indirect immunofluorescence tests and ELISA, respectively. These results show that S-M5(1-35) is immunogenic and evokes antibodies that recognize protective epitopes of type 5M protein on the surface of the streptococcus.

Three rabbits were also immunized with S-M5(26-35). The immune sera contained significant levels of antibodies against S-M5(1-35) and pep M5(Table III). In contrast to the S-M5(1-35) immune sera, S-M5(26-35) failed to evoke opsonic antibodies against type 5 streptococci, although the ELISA titers against pep M5 were equivalent for both sets of antisera. These results suggest that the antibodies raised against S-M5(26-35) bind to epitopes of pep M5 that may not be exposed on the surface of type 5 streptococci. In order to test this hypothesis, a particle phase ELISA was performed using whole type 5 streptococci as the test antigen. None of the S-M5(26-35) immune sera reacted with type 5 streptococci (Table III), confirming that the antibodies were directed against pep M5 epitopes that are not exposed on the type 5M protein in its native conformation on the surface of the organism.

Figure 1:
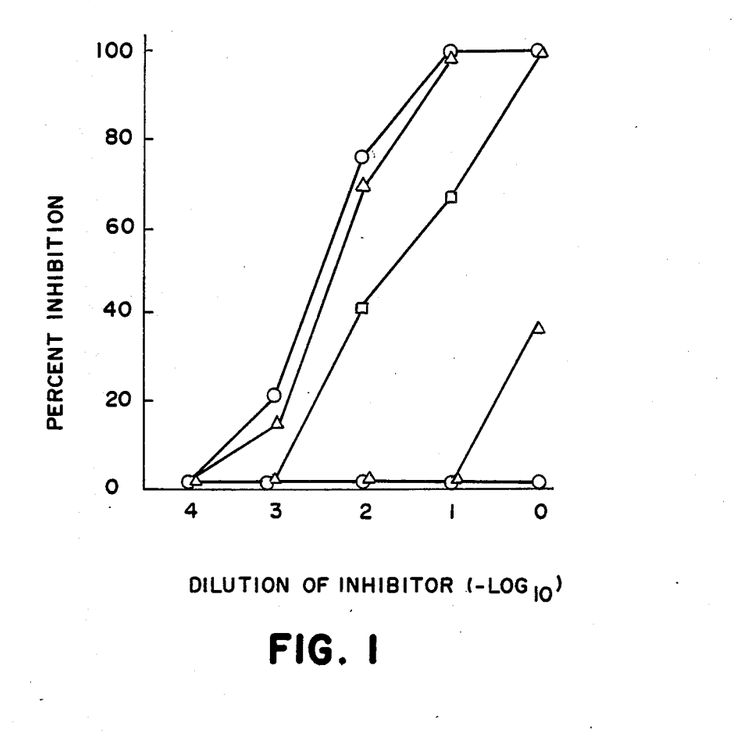

In order to determine the location of epitopes within S-M5(1-35) that evoked antibodies that reacted with native pep M5, ELISA inhibition tests were performed using the overlapping synthetic peptides as soluble inhibitors of S-M5(1-35) antibodies binding to pep M5 (FIG. 1). As expected, increasing concentrations of S-M5(1-35), the immunizing antigen, and pep M5, the solid phase test antigen, completely inhibit the binding of S-M5(1-35) antibodies to pep M5 (FIG. 1). S-M5(14-35) also completely inhibits the binding of antibodies to pep M5, suggesting that all of the "relevant" epitopes of S-M5(1-35), or those that evoke pep M5 reactive antibodies, reside in the S-M5(14-35) peptide, S-M5(21-35) partially inhibited antibody binding, whereas S-M5(26-35) had no effect (FIG. 1). Although these data were obtained using antiserum from one rabbit immunized with S-M5(1-35), similar patterns of inhibition were obtained with all six immune sera (data not shown).

Taken together, the data outlined thus far suggest that all of the protective epitopes of S-M5(1-35) reside between amino acid residues 14-26: first, all of the pep M5 antibodies evoked by S-M5(1-35) were inhibited by S-M5(14-35); second, none of the pep M5 reactive antibodies were inhibited by S-M5(26-35); and third, S-M5(26-35) evoked antibodies that were non-opsonic. ELISA inhibition experiments with S-M5(1-35) as the solid phase antigen and pep M5 as the soluble inhibitor revealed that not all of the antibodies were inhibited by pep M5, indicating that a portion of the antibodies were peptide specific (data not shown).

Figure 2:
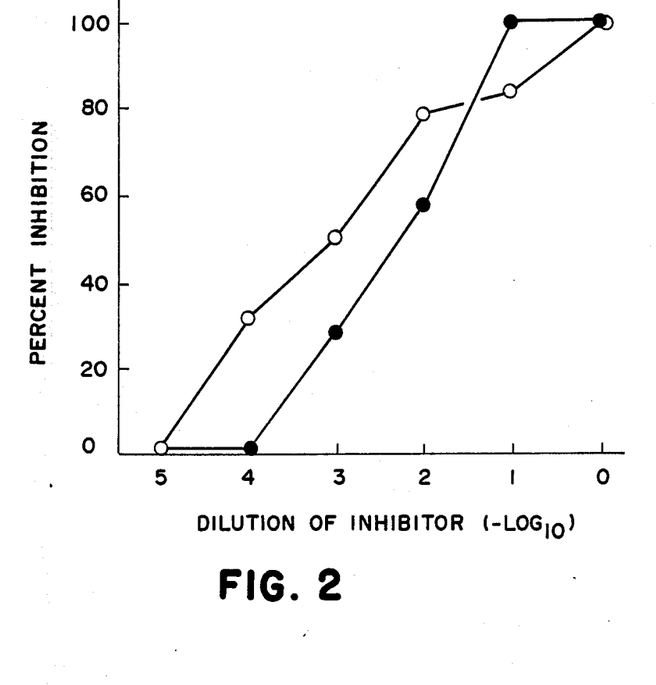

In order to test the hypothesis that the protective epitopes of S-M5(1-35) were located between amino acid residues 14-26, this peptide was synthesized and tested for its ability to inhibit type-specific and opsonic antibodies evoked by S-M5(1-35). Increasing concentrations of S-M5(14-26) completely inhibited S-M5(1-35) antibody binding to pep M5, as determined by ELISA inhibition studies (FIG. 2).

Opsonization inhibition assays were also performed to test for the presence of protective epitopes within S-M5(14-26). Opsonic antibodies against type 5 streptococci that were evoked by S-M5(1-35) were completely inhibited by S-M5(14-26) (Table IV). Total inhibition was also observed with S-M5(1-35), the immunogen, and pep M5, the natural peptide (Table IV). Opsonization of type 5 streptococci by the remaining S-M5(1-35) antisera was similarly inhibited by S-M5(14-26), indicating that the immunodominance of this region of the polypeptide was not the result of individual variation in immune responses.

The data presented thus far indicated that all of the antibodies evoked by S-M5(1-35) that reacted with pep M5 and type 5 streptococci were actually directed against the region represented by S-M5(14-26). To determine whether this region of type 5M protein was also immunodominant and evoked protective antibodies in animals immunized with whole type 5 streptococci, a situation that more closely resembles the immune response during natural infection, antiserum against intact type 5 organisms was affinity purified over a Sepharose-S-M5(1-35) column and the purified antibodies were used in opsonization inhibition assays (Table V). The S-M5(1-35) reactive antibodies opsonized type 5 streptococci, and the opsonization was completely inhibited by S-M5(1-35), pep M5, and S-M5(14-26). These data indicate that the immune response to the amino terminus of type 5M protein on the surface of the organism is similar to the immune response against S-M5(1-35). Although opsonization of type 5 streptococci by the affinity purified antibodies was completely inhibited by S-M5(14-26), control experiments using unfractionated antiserum clearly indicated the presence of additional opsonic epitopes that were not represented in S-M5(1-35) but that were present in pep M5 (Table V).

To determine the immunogenicity of S-M5(14-26), rabbits were immunized with the synthetic peptide that had been covalently linked to tetanus toxoid. S-M5(14-26) in the conjugated form proved to be an ineffective immunogen, possibly because the carrier molecule was covalently linked in such a way that it masked or altered the M protein epitopes. Therefore an additional peptide S-M5(14-26)C was synthesized which was covalently linked to KLH via the carboxyl-terminal cysteine residue (19, 20). All three rabbits immunized with this conjugate developed significant levels of antibodies against S-M5(14-26), S-M5(1-35), and pep M5, as measured by ELISA, and all three opsonized type 5 streptococci, as determined in vitro opsonization tests (Table VI).

The protective immunogenicity of S-M5(14-26)C and S-M5(1-35) was confirmed in indirect bactericidal tests (Table VII). Type 5 streptococci were rotated in whole human blood, to which was added either preimmune or immune serum. The immune sera against both synthetic peptides contained bactericidal antibodies as indicated by a significant reduction in colony forming units following a 3 hr. rotation in the test mixture (Table VII).

Because previous studies have shown that pep M5 contains not only type-specific but also cross-reactive epitopes (7-10, 23), the immune sera raised against the synthetic peptides was tested for the presence of antibodies directed against heterologous M proteins (Table VIII). S-M5(1-35) evoked significant levels of cross-reactive antibodies against pep M19, very low levels against pep M6, and none against pep M24, as measured by ELISA. The S-M5(14-26)C immune sera did not cross-react significantly with any of the heterologous antigens tested. Although S-M5(1-35) appeared to contain epitopes that were shared with pep M19, none of the antisera opsonized type 19 streptococci, suggesting that the cross-reactive antibodies may have been directed against nonprotective M protein epitopes of the surface of the organisms.

In addition, rabbits were immunized with an equimolar mixture of SM5(1-10)C, SM6(1-11)C and SM24(1-12)C linked through their COOH terminal cysteine residues to KLH via the bifunctional cross-linker SMCC. Each of three rabbits was injected with 100 nmol of synthetic peptide conjugate emulsified in CFA. The rabbits were bled as usual at 2-week intervals and the sera were tested by ELISA against pep M5, pep M6, pep M24 and by opsonization tests against types 5, 6, and 24 streptococci. Booster injections of the same dose of conjugate in saline were given at 4 and 8 weeks.

The antibody responses to the conjugated peptides at 10 weeks are shown in Table IX. All of the rabbits developed significant levels of antibody against at least two of the three pep M proteins. In addition, the rabbits developed opsonic antibodies against types 5, 6 and 24 streptococci.

Other advantageous characteristics of the invention will appear from the non-limiting examples which follow and with reference to FIG. 1 and 2 and the Tables illustrating the properties of the compounds of the invention.

EXAMPLE 1

Preparation of Streptococcal M Protein Peptides

Polypeptide fragments of M protein were isolated and purified from limited peptic digests of whole type 5, type 6, type 19 and type 24 group A *Streptococcus pyogenes* as previously described. (2-4) The purified polypeptides designated pep M5, pep M6, pep M19 and pep M24 were judged to be pure by sodium dodecyl-sulfate-gel electrophoresis and quantitative amino acid analysis.

Several overlapping peptide copies of the $NH_2$—terminal region of type 5M protein according to the amino acid sequence reported by Seyer et al, (17) were synthesized by the solid-phase method of Merrified, (18) as described (14). The synthetic peptides were purified by gel filtration on columns of Sephadex G50 and were additionally purified by reverse-phase high pressure liquid chromatography on Ultrasphere ODS2 (Whatman) (IBID). The purified peptides were analyzed for purity and composition by quantitative amino acid and automated Edman degradation to the penultimate amino acid residue (11, 13). The synthesized peptides are designated S-M5(1-35), S-M5(14-35), S-M5(21-35), S-M5(26-35), and S-M5(14-26). Additional peptides representing amino acid residues 14-26 of M5, synthesized with a carboxyl-terminal cysteine, S-M5(14-26)C, which allowed coupling to a carrier molecule using a bi-functional cross-linking reagent. SM5(1-10)C, SM6(1-11)C and SM24(1-12)C were synthesized in the same manner as S-M5(14-26)C.

EXAMPLE 2

Conjugation of Synthetic Peptides with Tetanus Toxoid

The synthetic peptides were conjugated to lysylated tetanus toxoid as described (14, 15). The conjugated peptides were stored frozen in 0.02M phosphate/0.15M Nacl. pH 7.4 (PBS) at $-70°$ C.

EXAMPLE 3

Conjugation of Synthetic Peptides with Keyhole Lympet Hemocyanin

S-M5(14-26)C, S-M5(1-10)C, SM6(1-11)C and SM24(1-12)C were conjugated to keyhole lympet hemocyanin (KLH) using succinimidyl 4-(N-maleimidomethyl) cyclohexane-1-carboxylate (SMCC) (Pierce, Rockford, IL) as described in Yoshitake, et al, (19), with the modifications of Rothbard et al., (20).

EXAMPLE 4

Immunization of Rabbits

New Zealand White rabbits were injected subcutaneously with 100 ug of the conjugated peptides, which had been emulsified in complete Freund's adjuvant (13-15). Blood was obtained before the initial injection and at 2 week intervals thereafter. At 4 and 10 weeks, the animals were given booster injections of 100 ug of the conjugate peptide in phosphate buffered saline (PBS, 0.02M phosphate, 0.15M NaCl, pH 7.4). Rabbit antiserum against the natural M5 protein was similarly prepared by immunizing with 100 ug doses of pep M5 or against whole type 5 streptococci by injection $10^9$ streptococci (heat-killed, 56° for 30 minutes) intracutaneously in 1 ml PBS, followed by intraperitoneal and intravenous booster injections.

EXAMPLE 5

M Protein Antibody Assays

Sera were tested for the presence of the M protein antibodies by an enzyme-linked immunosorbent assay (ELISA) using unconjugated synthetic peptides or pep M proteins as solid phase antigens, as previously described (7-22). In some cases ELISAs were performed using type 5 streptococci as particle phase test antigens (22). ELISA inhibition experiments were performed by incubating a constant dilution of antiserum with increasing concentrations of synthetic peptides or pep M5, as soluble inhibitors (15-21). Opsonic antibodies were detected by in vitro opsonophagocytic assays (3), and the peptide specificity of opsonic antibodies directed against type 5 streptococci was determined by opsonization inhibition tests using the synthetic peptides as soluble inhibitors (7, 13).

EXAMPLE 6

Affinity Purification of S-M5(1-35)

Antibodies raised against whole type 5 streptococci that reacted with S-M5(1-35) were affinity purified over a column of CH-Sepharose (Pharmacia, Inc., Uppsala, Sweden) to which S-M5(1-35) had been covalently linked (7, 9). The purified antibodies were dialyzed against PBS and concentrated to the original volume of serum by membrane filtration (YM 30 membrane; Amicon Corp., Scientific Systems Div., Lexington, MA).

EXAMPLE 7

Assays for heart cross-reactive antibodies

Each of the rabbit antisera was examined for immunologic cross-reactivity with human cardiac sarcolemmal membranes as described (10). In addition, they were assayed for cross-reactivity with rabbit muscle myosin (10) by ELISA.

The invention also encompasses biologically active compositions comprising the antigen and an immunostimulant and wherein the antigen is administered with the immunostimulant. CFA is one such immunostimulant. Other natural and synthetic immunostimulants are well known in the art. The administration need not be concurrent; one may precede the other, in part or all of it. What is important is that the two components are present in the system of the mammal concurrently.

The biological compositions of the invention can be in any suitable form for administration to the mammal, whether a human or animal. Such are known in the art.

Solid compositions for oral administration include compressed tablets, pills, powders and granules. In such solid compositions, at least one of the active ingredients is admixed with at least one inert diluent such as starch, calcium carbonate, sucrose or lactose. These compositions may also contain additional substances other than inert diluents, e.g. lubricating agents, such as magnesium stearate, talc and the like.

Liquid compositions for oral administration include pharmaceutically-acceptable emulsions, solutions, suspensions, syrups and elixirs containing inert diluents commonly used in the art, such as water. According to the invention, the compounds for oral administration also include capsules of absorbable material, such as gelatin, containing said active component with or without the addition or diluents or excipients.

Preparations according to the invention for parenteral administration include sterile aqueous-organic, and organic solutions, suspensions and emulsions. Examples of organic solvents or suspending media are propylene glycol, polyethylene glycol, vegetable oils, such as ethyl oleate. These compositions can also contain adjuvants such as stabilizing, preserving, wetting, emulsifying and dispersing agents. Aqueous compositions are by far preferred.

Preparations according to the invention for nasal administration include but are not limited to aerosols and inhalents. Such preparations are known in the art.

The percentage of active component in the said composition and method for causing the desired biological effect (e.g. immunooogical or hormonal inhibitory), can be varied so that a suitable dosage is obtained. The dosage administered to a particular patient is variable, depending upon the clinician's judgment using as the criteria: the route of administration, the duration of treatment, the size and condition of the patient, the potency of the active component, and the patient's response thereto. An effective dosage amount of active component can thus be determined best by the clinician considering all criteria and utilizing the best judgment on the patient's behalf. For practical considerations, the proportion may vary from about 0.01 to 20%, or higher, of active ingredient per composition. What is needed is that at least the minimum effective amount to give the desired effect be present.

The biological compositions of the invention can be used for vaccines to provide immunological protection against *Streptococcus pyogenes*. Vaccines are well known to those skilled in the art. What is intended is that the vaccines be used for immunological prophylaxis. The vaccines are administered by routes known to those in the art, including, inoculation, ingestion and nasal administration.

Other aspects of the invention will readily become apparent to one skilled in the art.

BIBLIOGRAPHY

1. Lancefield, R. C. 1962. Current knowledge of type-specific M antigens of group A streptococci. J. Immunol. 89:307.

2. Beachey, E. H., G. L. Campbell, and I. Ofek 1974. Peptide digestion of streptococcal M protein. II. Extraction of M antigen from group A streptococci with pepsin. Infect. Immun. 9:891.

3. Beachey, E. H., G. H. Stollerman, E. Y. Chiang, T. J. Chiang, J. M. Seyer, and A. H. Kang 1977. Purification and properties of M protein extracted from group A streptococci with pepsin: Covalent structure of the amino terminal region of type 24M antigen. J. Exp. Med. 145: 1469.

4. Beachey, E. H., J. M. Seyer, and A. H. Kang 1978. Repeating covalent structure of streptococcal M protein. Proc. Natl. Acad. Sci. USA 75:3163.

5. Beachey, E. H., G. H. Stollerman, R. H. Johnson, I. Ofek, and A. L. Bisno 1979. Human immune response to immunization with a structurally defined polypeptide fragment of streptococcal M protein. J. Exp. Med. 150:862.

6. Manjula, B. M., Seetharma-Acharya, S. M. Mische, T. Fairwell, and V. A. Fischetti 1984. The complete amino acid sequence of a biologically active 197-residue fragment of M protein isolated from type 5 group A streptococci. J. Biol. Chem. 259:3686.

7. Dale, J. B. and E. H. Beachey 1982. Protective antigenic determinant of streptococcal M protein shared with sarcolemmal membrane protein of human heart. J. Exp. Med. 156:1165.

8. Dale, J. B. and E. H. Beachey 1982. Protective antibody against a peptide fragment of type 5 streptococcal M protein cross-reacts with human heart tissue. Trans. Assoc. Am. Physicians 95:286.

9. Dale, J. B. and E. H. Beachey 1985. Multiple heart-cross-reactive epitopes of streptococcal M proteins. J. Exp. Med. 161:113.

10. Dale, J. B. and E. H. Beachey 1985. Epitopes of streptococcal M protein shared with cardiac myosin. J. Exp. Med. 162:583.

11. Beachey, E. H., J. M. Seyer, and A. H. Kang 1980. Primary structure of protective antigens of type 24 streptococcal M protein. J. Biol. Chem. 255:6284.

12. Beachey, E. H., J. M. Seyer, J. B. Dale, W. A. Simpson, and A. H. Kang 1981. Type-specific protective immunity evoked by synthetic peptide of *Streptococcus pyogenes* M protein. Nature 292:457–459.

13. Beachey, E. H., J. M. Seyer, J. B. Dale, and D. L. Hasty 1983. Repeating covalent structure and protective immunogenicity of native and synthetic polypeptide fragments of type 24 streptococcal M protein: Mapping of protective and nonprotective epitopes with monoclonal antibodies. J. Biol. Chem. 258:13250.

14. Beachey, E. H., A. Tartar, J. M. Seyer, and L. Chedid 1984. Epitope-specific protective immunogenicity of chemically synthesized 13-, 18- and 23-residue peptide fragments of streptococcal M protein. Proc. Natl. Acad. Sci. USA 81:2203–2207.

15. Dale, J. B., J. M. Seyer, and E. H. Beachey 1983. Type specific immunogenicity of a chemically synthesized peptide fragment of type 5 streptococcal M protein. J. Exp. Med. 158:1727–1732.

16. Beachey, E. H. and J. M. Seyer 1985. Protective and nonprotective epitopes of chemically synthesized peptides of the amino terminal region of type 6 streptococcal M protein. Submitted for publication.

17. Seyer, J. M., A. H. Kang, and E. H. Beachey 1980. Primary structural similarities between type 5 and 24M proteins of *Streptococcus pyogenes.* Biochem. Biophys. Res. Commun. 92:546.

18. Merrified, R. B. 1963. Solid phase peptide synthesis I. The synthesis of a tetrapeptide. J. Am. Chem. Soc. 85:2149.

19. Yoshitake, S., Y. Yamada, E. Ishikawa, and R. Masseyeff 1979. Conjugation of glucose oxidase from *Aspergillus niger* and rabbit antibodies using N-hydroxysuccinimide ester of N-(4-carboxycyclohexylmethyl) maleimide. Eur. J. Biochem. 101:395.

20. Rothbard, J. B., R. Fernandez, and G. K. Schoolnik 1984. Strain-specific and common epitopes of gonococcal pili. J. Exp. Med. 160:208.

21. Dale, J. B., I. Ofek, and E. H. Beachey 1980. Heterogeneity of type-specific and cross-reactive antigenic determinants within a single M protein of group A streptococci. J. Exp. Med. 151:1026.

22. Hasty, D. L., E. H. Beachey, W. A. Simpson and J. B. Dale 1982. Hybridoma antibodies against protective and nonprotective antigenic determinants of a structurally defined polypeptide fragment of streptococcal M protein. J. Exp. Med. 155:1010.

23. Dale, J. B. and E. H. Beachey 1984. Unique and common protective epitopes among different serotypes of group A streptococcal M proteins defined with hybridoma antibodies. Infect. Immun. 46:267.

24. Tainer, J. A., E. D. Getzoff, H. Alexander, R. A. Houghten, A. J. Olsen, R. A. Lerner, and W. A. Hendrickson 1984. The reactivity of anti-peptide antibodies is a function of the atomic mobility of sites in a protein. Nature 312:127.

25. Manjula, B. M. and Fischetti, V. A. 1980. Tropomyosin-like seven residue periodicity in three immunologically distinct streptococcal M proteins and its implications for the antiphagocytic property of the molecule. J. Exp. Med. 151:695.

26. Manjula, B. M. and V. A. Fischetti 1980. Studies on group a streptococcal M proteins: Purification of type 5M protein and comparison of its amino terminal sequence with two immunologically unrelated M protein molecules. J. Immunol. 124:261.

27. Phillips, G. N., P. F. Licker, C. Cohen, B. M. Manjula, and V. A. Fischetti 1981. Streptococcal M proteins: -helical coiled-coil structure and arrangement on the cell surface. Proc. Natl. Acad. Sci. USA 78:4689.

28. Chou, Y. nd D. Fasman 1978. Prediction of the secondary structure of proteins from their amino acid sequence. Adv. Enzymol. 47:45.

29. Stollerman, G. H., *Rheumatic Fever and Streptococcal Infection*, Grune and Stratton, New York, (1975).

30. Kaplan, M. H. and Meyersian, H., Lancet, I., 706 (1962).

31. Zabriskie, J. B. and Freimer, E. H., J. Med., 124, 661 (1966).

32. Kaplan, M. H., J. Immunol., 90, 595 (1963).

33. Audibert, F. et al., Nature 289, 593–594 (1981).

34. Hopp et al, Proc. Natl. Acad. Sci. USA, Vol. 78, No. 6, pps. 3824–28 (June 1981).

35. Cunningham, M. and E. H. Beachey, 1975, J. Immunol. 115:1002.

36. E. H. Beachey, J. M. Seyer and A. H. Kang, 1978, Proc. Natl. Acad. Sci. USA, 75:3163.

TABLE II

Type-specific, Opsonic Antibodies Evoked in Rabbits Immunized with SM5(1-35)

| Antiserum | ELISA titer against SM5(1-35) | pep M5 | Percent opsonization of type 5 streptococci |
|---|---|---|---|
| 8425 preimmune | <200 | <200 | 4 |
| 8425 12 wk | 25,600 | 3,200 | 86 |
| 8426 preimmune | <200 | <200 | 2 |
| 8426 12 wk | 51,200 | 12,800 | 86 |
| 8427 preimmune | <200 | <200 | 6 |
| 8427 12 wk | 51,200 | 6,400 | 96 |
| 8513 preimmune | <200 | <200 | 8 |
| 8513 14 wk | 25,600 | 3,200 | 86 |
| 8514 preimmune | <200 | <200 | 8 |
| 8514 14 wk | 25,600 | 6,400 | 84 |
| 8515 preimmune | <200 | <200 | 10 |
| 8515 14 wk | 25,600 | 6,400 | 66 |

TABLE III

Type-specific, Nonopsonic Antibodies Evoked in Rabbits Immunized with SM5(26-35)

| Antiserum | ELISA titer against SM5(1-35) | pep M5 | Type 5 streptococci | Percent phagocytosis of type 5 streptococci |
|---|---|---|---|---|
| 8437 preimmune | <200 | <200 | <200 | 8 |
| 8437 8 wk | 51,200 | 12,800 | <200 | 0 |
| 8438 preimmune | <200 | <200 | <200 | 0 |
| 8438 preimmune | 6,400 | 6,400 | <200 | 4 |
| 8439 preimmune | <200 | <200 | <200 | 0 |
| 8439 8 wk | 12,800 | 3,200 | <200 | 4 |

TABLE IV

Opsonization Inhibition of SM5(1-35) Antisera with SM5(14-26)

| Test serum | Inhibitor | Percent opsonization of type 5 streptococci |
|---|---|---|
| 8426 preimmune | none | 0 |
| 8426 10 wk | none | 42 |
|  | SM5(1-35) | 2 |
|  | SM5(14-26) | 0 |
|  | pep M5 | 4 |
| 8427 preimmune | none | 10 |
| 8427 10 wk | none | 44 |
|  | SM5(1-35) | 2 |
|  | SM5(14-26) | 2 |
|  | pep M5 | 8 |

TABLE V

Peptide Specificity of Opsonic Antibodies Evoked by Intact Type 5 Streptococci

| Antiserum | Inhibitor | Percent opsonization of type 5 streptococci |
|---|---|---|
| 7903 (affinity purified over SM5(1-35)) | none | 52 |
|  | SM5(1-35) | 10 |
|  | SM5(14-26) | 10 |

TABLE I

Chemically Synthesized Peptides Corresponding to the Amino Terminus of Pep M5

| Synthetic Peptide | Primary Structure |
|---|---|
| SM5(1-35) | AVTKGTINDPQAAKEALDKYELENHDLKTNNEGLK |
| SM5(14-35) | KEALDKYELENHDLKTNNEGLK |
| SM5(21-35) | ELENHDLKTNNEGLK |
| SM5(26-35) | DLKTNNEGLK |
| SM5(14-26) | KEALDKYELENHD |
| SM5(14-26)C | KEALDKYELENHDC |
| SM5(1-10)C | AVTKGTINDPC |

TABLE V-continued

Peptide Specificity of Opsonic Antibodies Evoked by Intact Type 5 Streptococci

| Antiserum | Inhibitor | Percent opsonization of type 5 streptococci |
|---|---|---|
| | pep M5 | 6 |
| 7903 (unfractionated) | none | 88 |
| | SM5(1-35) | 88 |
| | SM5(14-26) | 86 |
| | pep M5 | 10 |

TABLE VI

Type-Specific, Opsonic Antibodies Evoked in Rabbits Immunized with SM5(14-26)C

| | ELISA titer against | | | |
|---|---|---|---|---|
| Antiserum | SM5(1-35) | SM5 (14-26) | pep M5 | Percent phagocytosis of type 5 streptococci |
| 8516 preimmune | <200 | <200 | <200 | 8 |
| 8516 14 wk | 6,400 | 25,600 | 12,800 | 64 |
| 8517 preimmune | <200 | <200 | <200 | 8 |
| 8517 14 wk | 25,600 | 25,600 | 25,600 | 46 |
| 8518 preimmune | <200 | <200 | <200 | 8 |
| 8518 14 wk | 12,800 | 25,600 | 12,800 | 76 |

TABLE VII

Bactericidal Antibodies Against Type 5 Streptococci Evoked in Rabbits by SM5(1-35) and SM5(14-26)

| Antiserum | Immunizing antigen | Number of colonies of type 5 streptococci surviving after 3 hr growth in test mixture (inoculum = 6 colony forming units) |
|---|---|---|
| 8518 preimmune | SM5(14-26)C | >2000 |
| 8518 14 wk | | 210 |
| 8514 preimmune | SM5(1-35) | >2000 |
| 8514 14 wk | | 94 |
| 8329 preimmune | pep M5 | >2000 |
| 8329 14 wk | | 0 |

TABLE VIII

Type-Specific and Cross-Reactive Antibodies Evoked in Rabbits Immunized with SM5(1-35) or SM5(14-26)

| Antiserum | Immunizing antigen | ELISA titer against | | | |
|---|---|---|---|---|---|
| | | pep M5 | pep M6 | pep M19 | pep M24 |
| 8513 | SM5(1-35) | 3,200 | 200 | 1,600 | <200 |
| 8514 | SM5(1-35) | 6,400 | 400 | 1,600 | <200 |
| 8515 | SM5(1-35) | 6,400 | 400 | 3,200 | <200 |
| preimmune pool | | <200 | <200 | <200 | <200 |
| 8516 | SM5(14-26)C | 25,600 | 200 | 800 | <200 |
| 8517 | SM5(14-26)C | 51,200 | 200 | 400 | <200 |
| 8518 | SM5(14-26)C | 51,200 | 400 | 200 | <200 |
| preimmune pool | | <200 | <200 | <200 | <200 |

TABLE IX

Antibody Responses to Peptides at Ten Weeks

| Rabbit # | ELISA Against | | | Streptococcal Opsonization (%) against | | |
|---|---|---|---|---|---|---|
| | pep M5 | pep M6 | pep M24 | type 5 | type 6 | type 24 |
| 8613 | 1,600 | 12,800 | <200 | 2 | 88 | 2 |
| 8624 | <200 | 12,800 | 3,200 | 2 | 84 | 88 |
| 8615 | 1,600 | 6,400 | 3,200 | 72 | 90 | 94 |

We claim:

1. A synthetic polypeptide which elicits opsonobactericidal antibodies against pep M5 and which is not serologically cross-reactive with tissue antigens of the heart, which polypeptide has the amino acid sequence X-Glu-Ala-Leu-Asp-Lys-Tyr-Glu-Leu-Glu-Asn-His-Y wherein
X is Lys- or A-Val-Thr-B-Gly-Thr-Ile-C-Asp-Pro-Gln-D-Ala-Lys wherein
A is Ala or Thr,
B is Lys or Arg,
C is Asn or Ser, and
D is Ala or Arg; and
wherein
Y is
-Asp,
-Asp-Cys or
-Asp-Leu-Lys-Thr-E-Asn-Glu-Gly-Leu-Lys
wherein E is Asn or Lys.

2. The synthetic polypeptide of claim 1 which is

Ala—Val—Thr—Lys—Gly—Thr—Ile—Asn—Asp—Pro—Gln—Ala—Ala—Lys—Glu—Ala—Leu—Asp—Lys—Tyr—Glu—Leu—Glu—Asn—His—Asp—Leu—Lys—Thr—Asn—Asn—Glu—Gly—Leu—Lys.

3. The synthetic polypeptide of claim 1 which is

Lys-Glu-Ala-Leu-Asp-Lys-Tyr-Glu-Leu-Glu-Asn-His-Asp-Leu-Lys-Thr-Asn-Asn-Glu-Gly-Leu-Lys.

4. The synthetic polypeptide of claim 1 which is

Lys-Glu-Ala-Leu-Asp-Lys-Tyr-Glu-Leu-Glu-Asn-His-Asp.

5. The synthetic polypeptide of claim 1 which is

Lys-Glu-Ala-Leu-Asp-Lys-Tyr-Glu-Leu-Glu-Asn-His-Asp-Cys.

6. A synthetic antigen conjugate which comprises a polyvalent carrier covalently linked to the polypeptide of claim 2, which antigen elicits type M5 specific opsonic antibodies to *Streptococcus pyogenes* and which is not serologically cross-reactive with tissue antigens of the heart.

7. The synthetic antigen of claim 6 wherein the carrier is tetanus toxoid.

8. The synthetic antigen of claim 6 wherein the carrier is keyhole limpet hemocyanin.

9. An immunogenic biological composition which comprises a biologically acceptable diluent, an immunostimulant and in an amount sufficient to elicit opsonic antibodies to *Streptococcus pyogenes* and not be serologically cross-reactive with tissue antigens of the heart, the synthetic antigen of claim 6.

10. The immunogenic biological composition of claim 10 wherein the immunostimulant is complete Freund's adjuvant or a synthetic immunostimulant.

11. A method for controlling streptococcal infections in a mammal which comprises administering to a mammal in a dose sufficient to control *Streptococcus pyogenes,* the composition of claim 9, and controlling *Streptococcus pyogenes* in said mammal.

12. A synthetic polypeptide having the amino acid sequence

Glu-Leu-Glu-Asn-His-Asp-Leu-Lys-Thr-Asn-Asn-Glu-Gly-Leu-Lys.

13. A synthetic antigen conjugate which comprises a polyvalent linkable carrier covalently linked to the polypeptide of claim 12 which antigen is able to evoke high titers of ELISA antibody against itself.

14. A synthetic polypeptide having the amino acid sequence

Asp-Leu-Lys-Thr-Asn-Asn-Glu-Gly-Leu-Lys.

15. A synthetic antigen conjugate which comprises a polyvalent linkable carrier covalently linked to the polypeptide of claim 14 which antigen is able to evoke high titers of ELISA antibody against itself.

16. A synthetic polypeptide having the amino acid sequence

A-Val-Thr-B-Gly-Thr-Ile-C-Asp-Pro-Cys.

wherein

A is Ala or Thr,

B is Lys or Arg and,

C is Ala or Arg.

17. The synthetic polypeptide of claim 16 which is

Ala-Val-Thr-Lys-Gly-Thr-Ile-Asn-Asp-Pro-Cys.

18. A synthetic antigen conjugate which comprises a polyvalent linkable carrier covalently linked to the polypeptide of claim 16 which antigen is able to elicit type M5 specific opsonic antibodies to pep M5 and which is not serologically cross-reactive with tissue antigens of the heart.

19. The synthetic antigen of claim 18 wherein the polyvalent linked carrier is a natural protein carrier.

20. The synthetic antigen of claim 19 wherein the carrier is keyhole limpet hemocyanin.

21. An immunogenic biological composition which comprises a biologically acceptable diluent, an immunostimulant and in an amount sufficient to elicit opsonic antibodies to *Streptococcus pyogenes* and not be serologically cross-reactive with tissue antigens of the heart, the synthetic antigen of claim 18.

22. A method for controlling streptococcal infections in a mammal which comprises administering to a mammal in a dose sufficient to control *Streptococcus pyogenes,* the composition of claim 21, and controlling *Streptococcus pyogenes* in said mammal.

23. A vaccine which comprises a biologically acceptable diluent, an immunostimulant and in an amount sufficient to elicit opsonic antibodies to *Streptococcus pyogenes* and not be serologically cross-reactive with tissue antigens of the heart, the synthetic antigen of claim 13.

24. A vaccine which comprises a biologically acceptable diluent, an immunostimulant and in an amount sufficient to elicit opsonic antibodies to *Streptococcus pyogenes* and not be serologically cross-reactive with tissue antigens of the heart, the synthetic antigen of claim 15.

25. A synthetic polypeptide having the amino acid sequence

Arg-Val-Phe-Pro-Arg-Gly-Thr-Val-Glu-Asn-Pro-Cys.

26. A synthetic antigen conjugate which comprises a polyvalent linkable carrier covalently linked to the polypeptide of claim 25 which antigen is able to evoke high titers of ELISA antibody against itself.

27. A synthetic polypeptide having the amino acid sequence

Val-Ala-Thr-Arg-Ser-Gln-Thr-Asp-Thr-Ser-Glu-Lys-Cys.

28. A synthetic antigen conjugate which comprises a polyvalent linkable carrier covalently linked to the polypeptide of claim 27 which antigen is able to evoke high titers of ELISA antibody against itself.

* * * * *